United States Patent
Gutierrez

[11] Patent Number: 5,819,769
[45] Date of Patent: Oct. 13, 1998

[54] DENTAL FLOSS SYSTEM

[76] Inventor: Gregorio Gutierrez, 2462 18th St., Sacramento, Calif. 95820

[21] Appl. No.: 803,267

[22] Filed: Feb. 20, 1997

[51] Int. Cl.⁶ .................................................... A61C 15/00
[52] U.S. Cl. .................................... 132/327; 132/324
[58] Field of Search .................. 132/323, 324, 132/325, 326, 327

[56] References Cited

U.S. PATENT DOCUMENTS

| D. 251,074 | 2/1979 | Schiff . | |
|---|---|---|---|
| 1,110,680 | 9/1914 | Gambel | 132/325 |
| 1,465,669 | 8/1923 | Hochstadter | 132/324 |
| 1,916,653 | 7/1933 | Bodde | 132/326 |
| 2,187,442 | 1/1940 | Beach | 132/326 |
| 2,289,625 | 7/1942 | Burns | 132/324 |
| 3,592,203 | 7/1971 | Johnson | 132/323 |
| 4,522,216 | 6/1985 | Bunker | 132/323 |
| 4,753,254 | 6/1988 | McCullough et al. | 132/324 |
| 4,827,952 | 5/1989 | Kos | 132/323 |
| 5,067,503 | 11/1991 | Stile | 132/324 |
| 5,105,840 | 4/1992 | Giacopuzzi | 132/326 |
| 5,123,432 | 6/1992 | Wyss . | |
| 5,197,498 | 3/1993 | Stewart | 132/327 |
| 5,495,863 | 3/1996 | Bergman . | |
| 5,538,023 | 7/1996 | Oczkowski et al. . | |
| 5,657,780 | 8/1997 | Giacopuzzi | 132/326 |
| 5,664,592 | 9/1997 | Regnier | 132/327 |

FOREIGN PATENT DOCUMENTS

| 522909 | 4/1931 | Germany | 132/323 |
|---|---|---|---|
| 3920256 | 2/1990 | Germany | 132/323 |

*Primary Examiner*—Todd E. Manahan
*Attorney, Agent, or Firm*—Thomas R. Lampe

[57] ABSTRACT

A dental floss system includes a dental floss holder including two pivoted holder elements. Floss is positioned in slots formed at ends of the holder elements. The holder incorporates mechanism for advancing the floss relative to the holder to present clean lengths of floss to the user.

16 Claims, 7 Drawing Sheets

Fig. 33 ance with the teachings of the present invention and holding dental floss;

DENTAL FLOSS SYSTEM

TECHNICAL FIELD

This invention relates to a dental floss system, more particularly, to a dental floss holder and dental floss for employment with the holder. Even more particularly, the invention is concerned with a system which readily and conveniently presents dental floss for use by an individual flossing his or her teeth.

BACKGROUND OF THE INVENTION

A great many types of holders are known in the prior art for holding dental floss and enabling the user to manipulate the floss in his or her teeth for dental hygiene purposes. Some holders are of the permanent type, being retained by the individual after use and incorporating arrangements for replacing or advancing dental floss to present clean floss for the next use. Other types of floss holders exist in which the floss is permanently attached to the holder, with the holder and floss being discarded after use. In other words, these latter types of devices are so-called "disposable" products. Such products are essentially wasteful of resources and environmentally unfriendly.

On the other hand, many holders of the "permanent" type are characterized by their relative complexity and/or high expense. Furthermore, a common characteristic of such holders is that they are inconvenient to use, particularly with regard to repositioning or replacing floss after use.

The following patents are considered generally representative of the current state of the dental floss holder art: U.S. Pat. No. 5,538,023, issued Jul. 23, 1996; U.S. Pat. No. 5,123,432, issued Jun. 23, 1992; U.S. Pat. No. 5,495,863, issued Mar. 5, 1996; U.S. Pat. No. Des 251,074, issued Feb. 13, 1979.

DISCLOSURE OF INVENTION

The present invention relates to a dental floss system including a dental floss holder. A number of holder embodiments are disclosed and claimed herein, including a dental floss holder having a double-ended, elongated first holder element including a floss-holding end and a manually graspable end.

Also incorporated in the holder is a double-ended, elongated second holder element including a floss-holding end and a manually graspable end.

Pivot means interconnects the holder elements. At least one of the holder elements is rotatably moveable about the pivot axis defined by the pivot means to vary the distance between the floss-holding ends of the holder elements.

Floss securement means is provided for temporarily securing dental floss to the dental floss holder at spaced locations on the dental floss with the dental floss extending between the floss-holding ends of the holder elements.

In a preferred embodiment, a protruding guide member is located adjacent to a slot on at least one of the holder elements for bearing against the dental floss when the dental floss is being applied to the dental floss holder to guide the dental floss into the adjacent slot.

The system of the present invention also encompasses dental floss of a specialized character which is for the purpose of being utilized with a dental floss holder. The dental floss comprises a length of flexible dental floss material having first and second ends. A plurality of enlargements for engagement by a dental floss holder are attached to the length of flexible dental floss material between the first and second ends.

Other features, advantages, and objects of the present invention will become apparent with reference to the following description and accompanying drawings.

MODES FOR CARRYING OUT THE INVENTION

Referring now to FIGS. 1–10, a preferred embodiment of the invention is illustrated. The dental floss holder of this embodiment includes two double-ended, elongated holder elements 10 and 12 which are pivoted about a pivot member 14. At one end thereof pivot member 14 is in the form of a projection 16 which is used to secure or tie down dental floss 18 in a manner which will be described below. Projection 16 is generally in the shape of a disc having a groove 20 extending about the periphery thereof. Groove 20 is for the purpose of accommodating dental floss when the dental floss is tied down or secured thereto.

Figure 1:
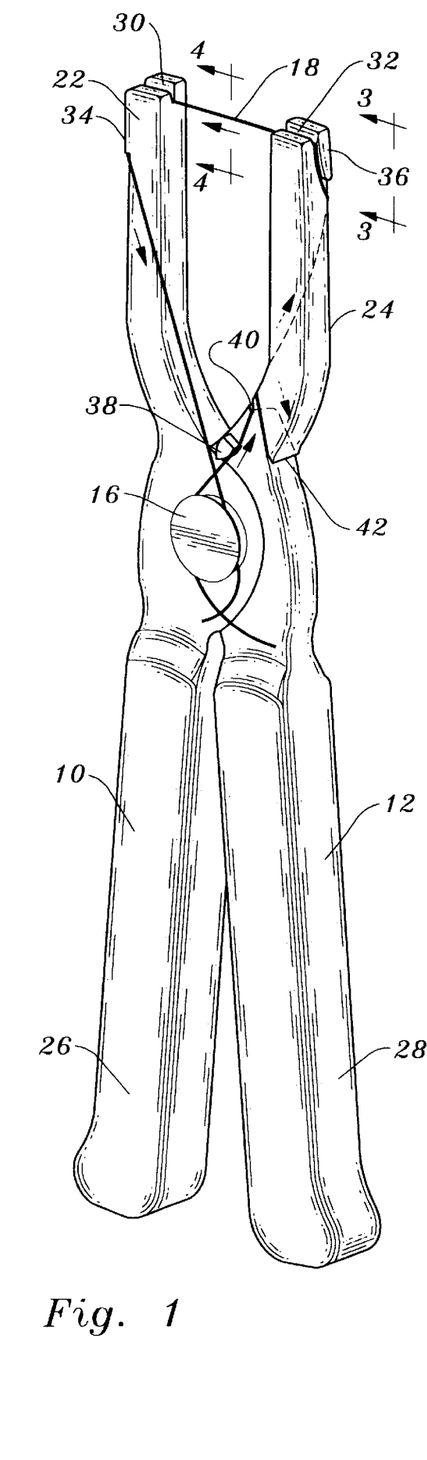
FIG. 1 is a perspective view of a first embodiment of a dental floss holder constructed in accordance with the teachings of the present invention and holding dental floss.
Figures 2, 3, 4:
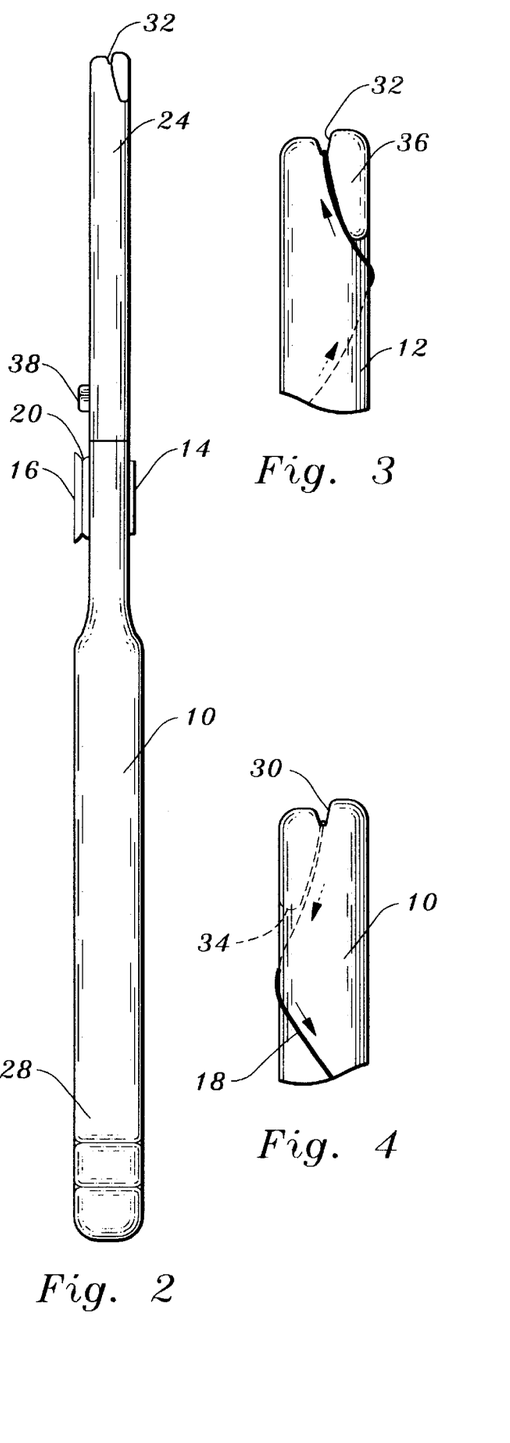
FIG. 2 is a side view of the dental floss holder.
FIG. 3 is an enlarged view of a portion of the dental floss holder taken along the line 3—3 in FIG. 1.
FIG. 4 is a view similar to FIG. 3 but taken along the line 4—4 in FIG. 1.

Holder elements 10, 12 respectively include floss-holding ends 22, 24 and manually graspable ends 26, 28. It will be appreciated that movement of the manually graspable ends toward one another will move the floss-holding ends 22, 24 away from one another.

A slot 30 is located at the distal end of floss-holding end 22 and a slot 32 is located at the distal end of floss-holding end 24, the slots extending across the full lengths of their respective floss-holding ends. A guide member 34 protrudes from floss-holding end 22 adjacent to slot 30 and a protruding guide member 36 of like construction extends from floss-holding end 12 adjacent to slot 32.

A third protruding guide member 38 protrudes from holder element 12 at a location near projection 16. Formed in holder element 12 at locations adjacent to guide member 38 are slots 40, 42. The slots 40, 42 are located on opposed sides of the holder element 12 between projection 16 and the floss-holding ends thereof.

Figures 9, 10:
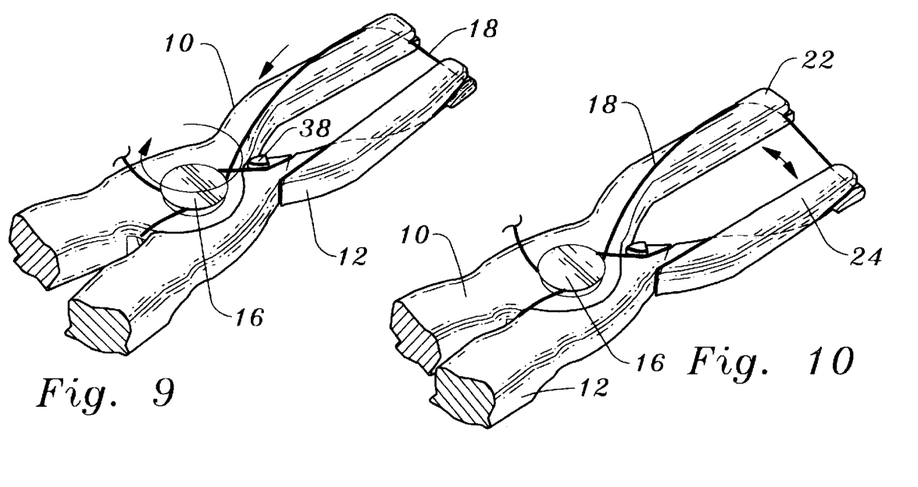

FIGS. 1 and 10 illustrate dental floss 18 fully applied to the holder; that is, the dental floss is positioned and held by the holder for use by an individual when flossing his or her teeth.

Figures 5, 6, 7, 8:
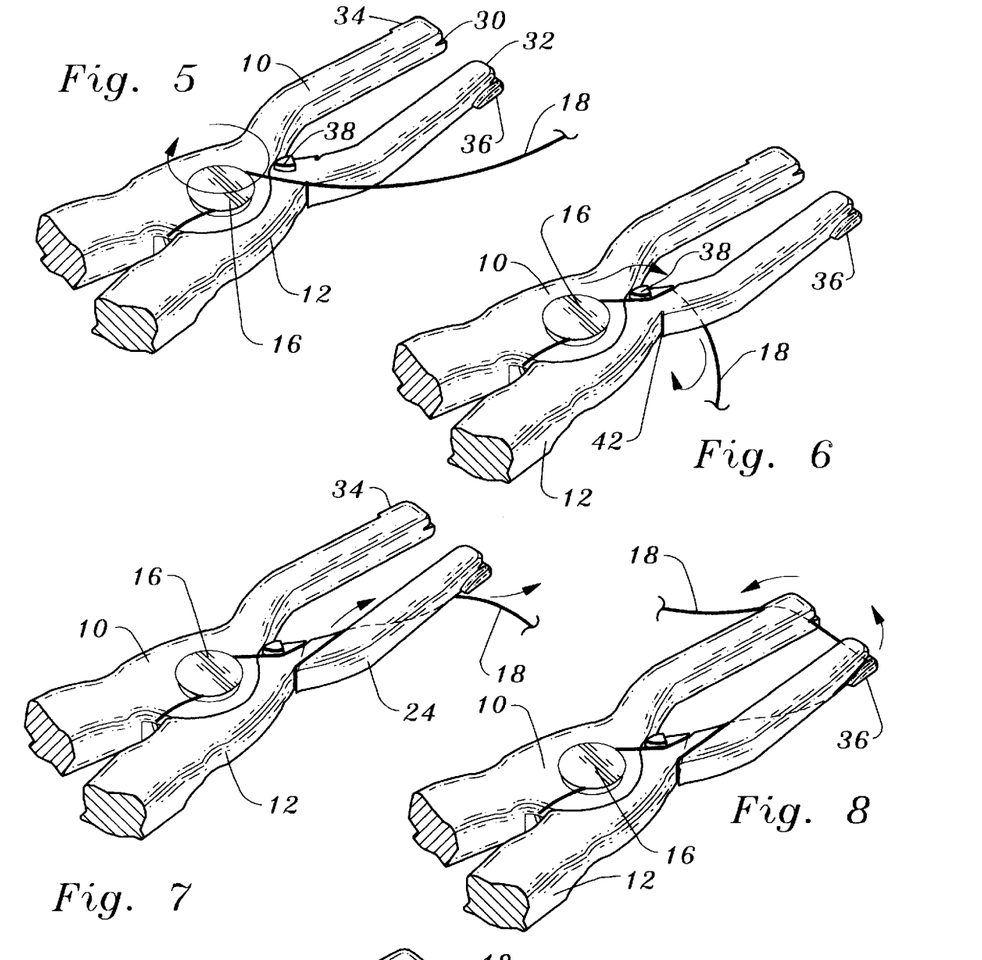
FIGS. 5 through 10 are perspective views illustrating a segment of the dental floss holder and illustrating in diagrammatic fashion application of dental floss thereto, sequential steps of the operation being shown in the sequential figures.

The first step when applying dental floss to the holder is shown in FIG. 5 wherein an end of floss 18 is wrapped clockwise about projection 16 within the circular notch thereof.

FIG. 6 illustrates the floss positioned against guide member 38 and into slot 40. The floss is wrapped about the holder element 12 (as shown by the arrow in FIG. 6) and positioned in slot 42. This operation creates a reserve loop of floss.

Next, the floss is passed under and around floss-holding end 24 and then brought around as shown by the arrow in FIG. 7 to be placed in engagement with guide member 36. The floss is then passed through slots 32, 30 as shown in FIG. 8. The floss is placed into engagement with guide member 34 and brought down along the front of holder element 10 as shown in FIG. 9 to projection 16. The free floss end is then wrapped about the projection 16 within the groove thereof to secure the floss in place.

By manually moving the manually graspable ends 26, 28 of the holder together the floss-holding ends 22, 24 are drawn apart as shown in FIG. 10 to tighten the floss. During use, the floss-holding ends 22, 24 may be moved further apart to maintain tension on the floss if the floss stretches during use.

An important aspect of the embodiment shown in FIGS. 1–10 is the formation of a reserve loop of floss between slots 40, 42 when the floss is initially applied to the holder. A user may utilize such reserve loop to position a new length of the dental floss between the floss-holding ends 22, 24 when fresh floss is to be presented for use. This is accomplished by untying the second (last) tie down of the floss to the projection 16, unlooping the reserve loop from between the slots 40, 42 and rethreading the floss through the slots 30, 32 before retying the loose floss end. This will position fresh floss between the floss-holding ends of the holder. It will be appreciated that more than one reserve loop may be formed between the slots 40, 42 to permit floss repositioning a number of times, the user simply unwinding one loop per advancement.

FIGS. 11–15 illustrate another embodiment of dental floss-holder constructed in accordance with the teachings of the present invention. Here the holder elements are designated by reference numerals 10A, 12A, the floss-holding ends thereof respectively designated by reference numerals 22A, 24A and the manually graspable ends thereof by reference numerals 26A, 28A. The holder elements are pivoted about pivot member 14A including a projection 16A having a circular groove of the type employed in the dental floss-holder of FIG. 1.

Figures 11, 12:
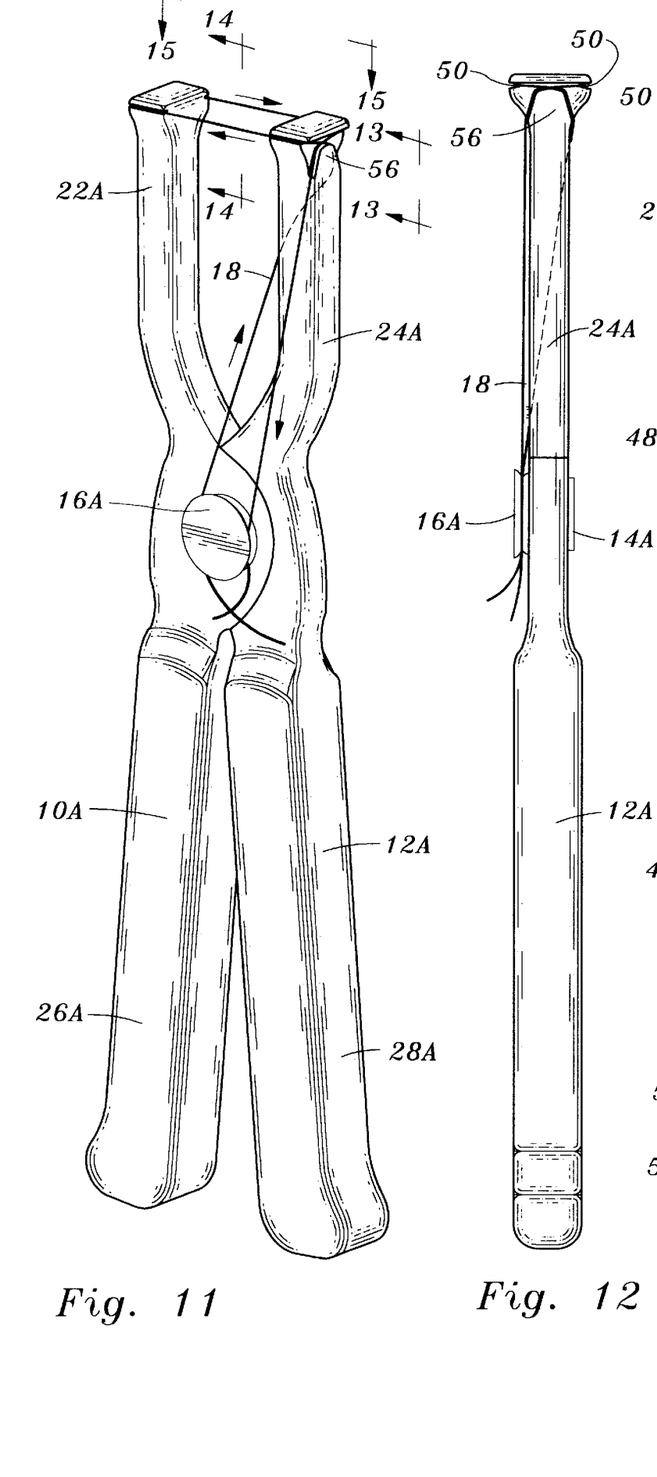
FIG. 11 is a view similar to FIG. 1 but illustrating a second embodiment of dental floss holder holding dental floss.
FIG. 12 is a side view illustrating the second dental floss holder embodiment and floss.
Figure 13:
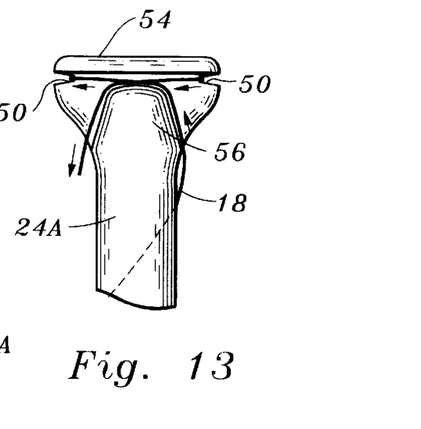
FIG. 13 is an enlarged view of that portion of the dental floss holder taken along line 13—13 in FIG. 11.
Figure 14:
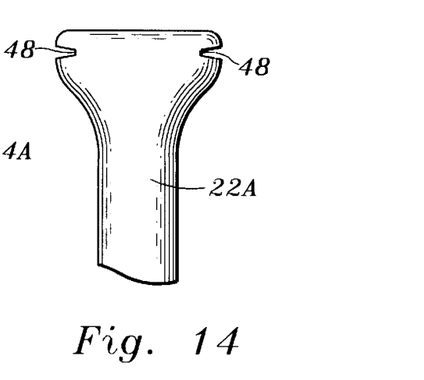
FIG. 14 is an enlarged view of that portion of the dental floss holder taken along the line 14—14 in FIG. 11.
Figure 15:
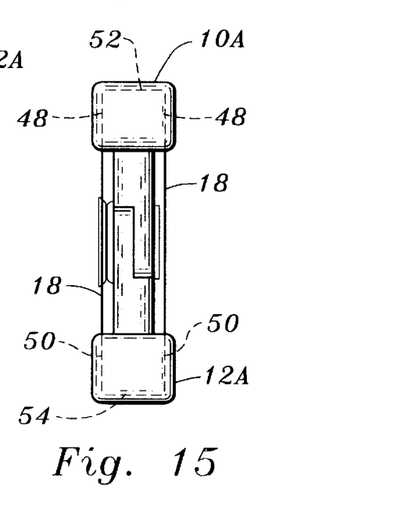
FIG. 15 is a top view of the dental floss holder and dental floss as taken in the direction of line 15—15 in FIG. 11.

Floss-holding ends 22A, 24A each define a pair of slots, the slots of each pair of slots being positioned on opposed sides of the holder element defining the pair of slots. The slots of floss-holding end 22A are designated by reference numeral 48 and the opposed slots defined by floss-holding end 24A are designated by reference numeral 50.

In the arrangement illustrated, the distal ends of the floss-holding ends also form connector slots 52, 54 interconnecting slots 48 and slots 50, respectively. A protruding guide member 56 projects outwardly from floss-holding end 24A just below connector slot 54 and adjacent to slots 50. The protruding or projecting guide member 56 is utilized to properly position or guide the dental floss during threading and use.

FIGS. 11–13 and 15 illustrate floss 18 positioned on this embodiment of the dental floss-holder. Arrows in FIGS. 11 and 13 illustrate the sequence employed when applying the floss to the holder. First, one end of the floss is wrapped about projection 16A and directed upwardly and about floss-holding end 24A over guide member 56. The floss is then directed through one of slots 50 to one of the slots 48 and thence around the back of floss-holding end 22A in slot 52, through the other slot 48, and then through the remaining empty slot 50 of floss-holding end 24A. The floss then proceeds over guide member 56 down to the projection 16A where it is wrapped thereabout. The floss may be tensioned between floss-holding ends 22A, 24A merely by bringing the manually graspable ends 26A, 28A closer together.

With this arrangement the dental floss is looped between and about the floss-holding ends and includes two spaced, straight dental floss loop segments extending between the floss-holding ends. A person cleaning his or her teeth has the option of using either of these lengths during the flossing operation.

FIGS. 16–19B disclose another embodiment of the invention. The holder elements of the subject dental floss holder are designated by reference numerals 10B, 12B. The manually graspable ends of holder elements 10B, 12B are designated respectively by reference numerals 26B, 28B and the floss-holding ends thereof are designated to respectively by reference numerals 22B, 24B. Slots 30B, 32B are respectively formed at the distal ends of floss-holding ends 22B, 24B and extend thereacross.

Figures 16, 17, 18, 19, 19A, 19B:
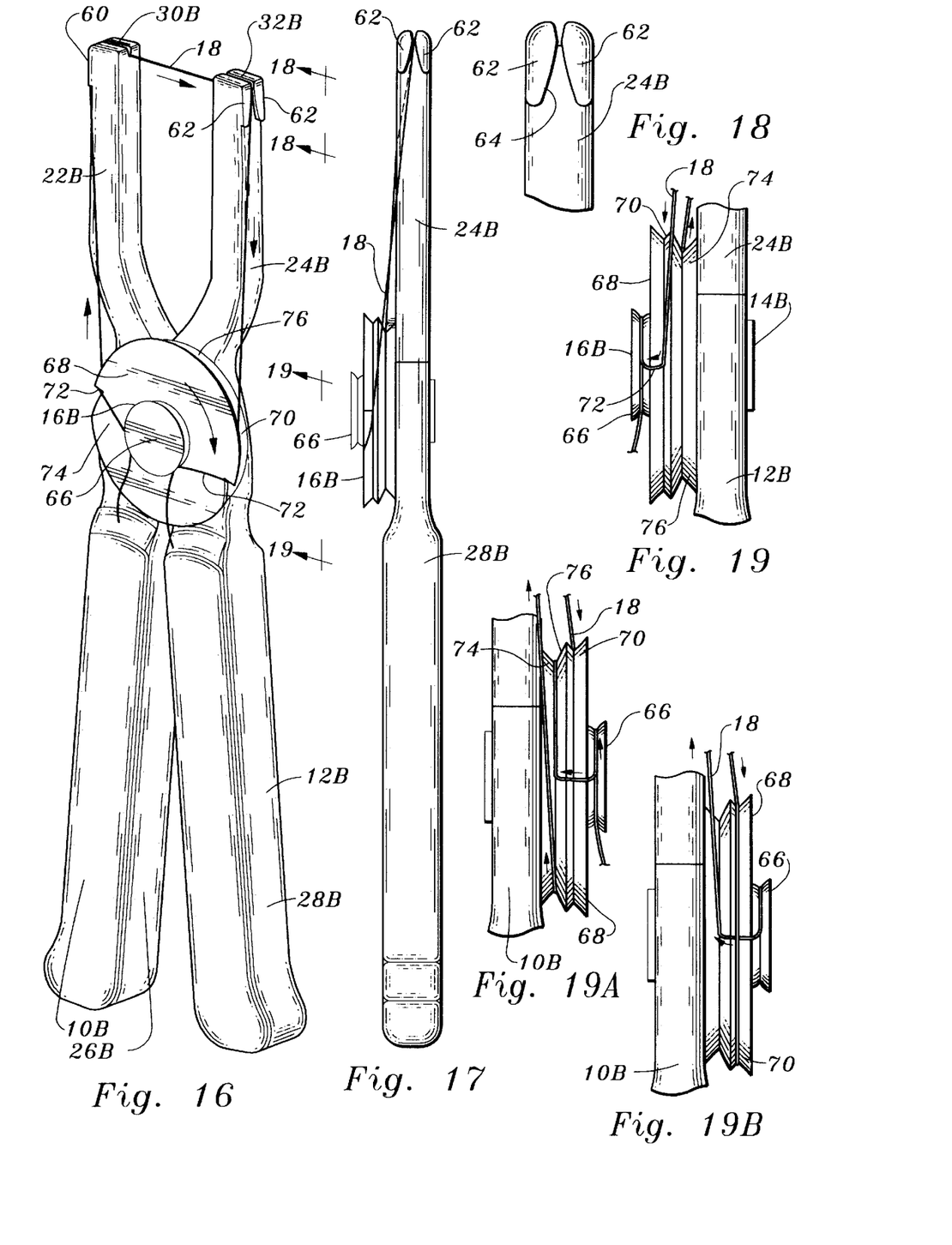
FIG. 16 is a view similar to FIG. 1 but illustrating a third embodiment of dental floss holder constructed in accordance with the teachings of the present invention with dental floss.
FIG. 17 is a side view of the holder and floss shown in FIG. 16.
FIG. 18 is an enlarged view illustrating a portion of the dental floss holder of FIG. 16 as taken along the line 18—18 in FIG. 16.
FIG. 19 is an enlarged side view illustrating a portion of the dental floss holder of FIG. 16 denoted by lines 19—19.
FIG. 19A illustrates the same portion of the dental floss holder as FIG. 19 but with the view thereof as seen from the opposed side of the dental floss holder.
FIG. 19B is a view similar to that of 19A but illustrating the structure and floss in the respective positions assumed thereby after rotation of a floss winding member.

Two guide members protrude outwardly from each of floss-holding ends 22B, 24B. Only one such guide member, guide member 60, is illustrated for floss-holding end 22B. The guide members associated with floss-holding end 24B are designated by reference numeral 62. Each pair of guide members forms a downwardly extending notch therebetween which communicates with the respective slot. The notch associated with slot 32B is designated by reference numeral 64.

The dental floss holder under discussion incorporates a winding system for advancing floss to reposition it relative to the floss-holding ends thereof. More particularly, the projection 16B of the pivot member 14B is of a particular nature and is rotatable relative to the other structure of the dental floss holders.

Projection 16B is of integral construction and includes an outer disc-shaped securement element 66 having an outer circular groove. In addition, affixed to securement member 66 is a floss engaging and winding member 68 which has a floss winding groove 70 defining an arc comprising a segment of a circle. The bottom of the member 68 (as viewed in FIG. 16) forms floss engagement surfaces 72 located where the member 68 terminates.

Integral with floss engaging and winding member 68 is a second floss engaging and winding member 74 defining a circular winding groove 76. It is to be noted that the diameter of winding groove 74 is less than the diameter of winding groove 70.

Attachment of floss 18 to the dental floss holder of FIGS. 16–19B is accomplished first by wrapping an end of the floss about securement member 66. The floss engages one of the floss engaging surfaces 72 of member 68 and then is wound about member 76 in groove 74. Then the floss is moved upwardly along floss-holding end 22B through the notch defined by guide members 60 and thence through slot 30B, across the space between the floss-holding ends and then through slot 32B.

After passing downwardly through notch 64 defined by guide members 62, the floss is positioned in winding groove 70 of member 68 as shown in FIGS. 17, 19 and 19A. Next the floss is located under floss engaging surface 72 and wrapped about securement member 66 to secure the floss in place.

The user can now employ the floss extending between floss-holding ends 22B, 24B to clean his or her teeth. As the user flosses, the floss-holding ends will tend to move further and further apart because the floss will stretch as it is utilized.

When the user wishes to advance the floss and present a fresh segment of the floss between the floss-holding ends 22B, 24B, the projection 16B is turned clockwise relative to the holder elements as shown by the arrow in FIG. 16. This will cause the floss on the second floss engaging and winding member 76 to unwind while the other end of the floss is wound onto floss engaging and winding member 68. Since the diameter of the groove of member 68 is greater than that of the groove of member 76 more floss will be wound onto the projection than is unwound therefrom. This results in the floss-holding ends being moved closer together while a fresh length of floss is positioned therebetween, it being appreciated that one does not want the floss-holding ends too far apart when flossing which can occur, for example, from stretching of the floss. FIG. 19B may be referred to show the condition of the apparatus after floss advancement has occurred due to one complete revolution of projection 16B having taken place.

Claims 20–24 disclose yet another embodiment of the dental floss holder constructed in accordance with the teachings of the present invention. This dental floss holder differs from that of the embodiment just described in a number of respects. In this embodiment of the invention the pivot member includes a projection 16C incorporating two relatively moveable components. In particular, the projection 16C includes a securement member 80 having a handle 82 affixed thereto. Securement member 80 is affixed to a stub shaft 84 which extends inwardly therefrom and is rotatably seated within the other end of the pivot member. The securement member 80 is operatively associated with a ratchet mechanism within the confines of the unit. More particularly, a ratchet wheel 85 is affixed to securement member 80 and is rotatable therewith. A pawl 86 is associated with the ratchet wheel to permit rotation of the securement member 80 in one rotational direction only.

Figures 20, 21, 22, 23, 24, 25, 25A:
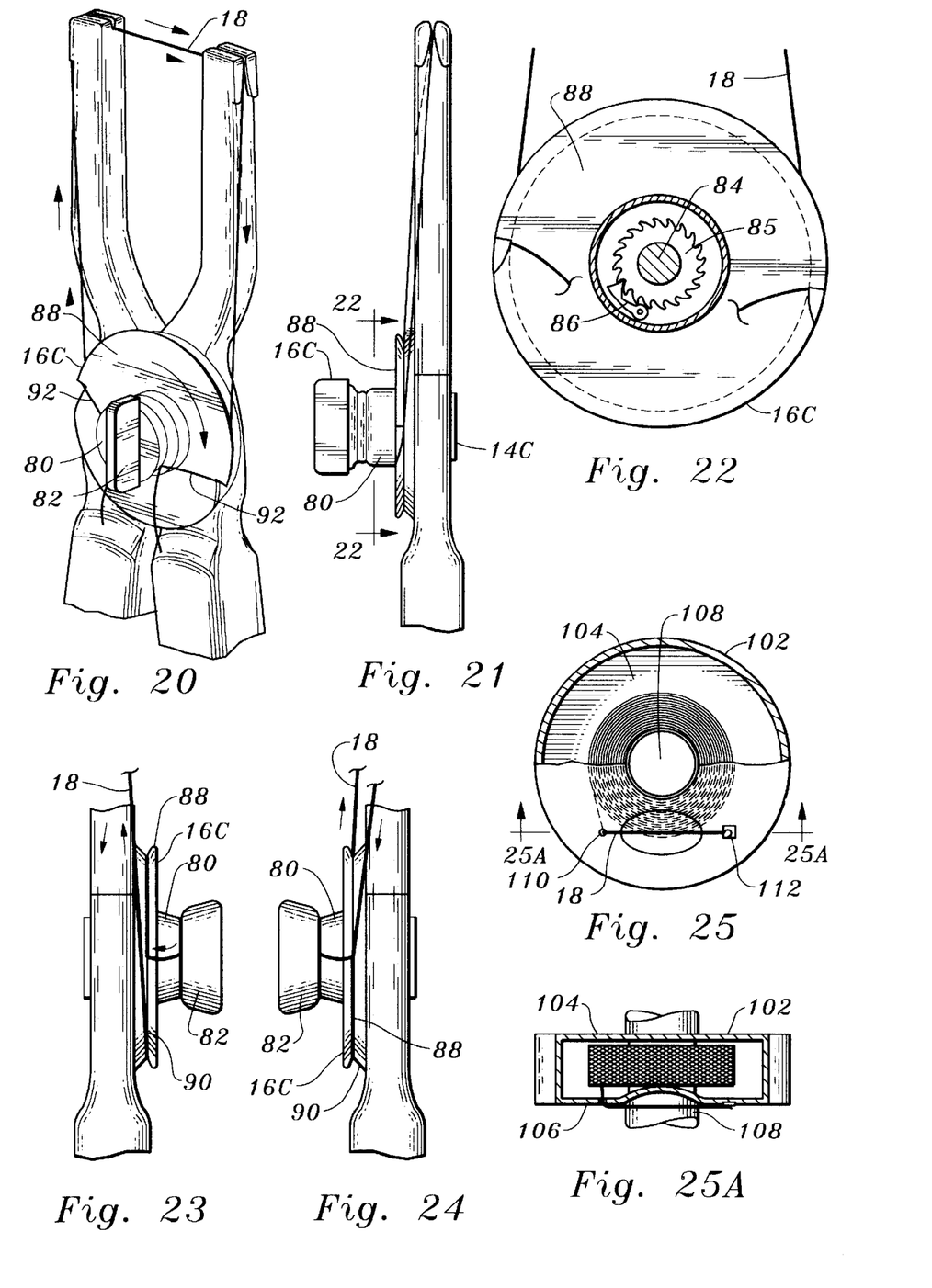
FIG. 20 is a perspective view of a portion of a fourth embodiment of dental floss holder with floss attached thereto.
FIG. 21 is a partial, side view of the dental floss holder of FIG. 20 and floss.
FIG. 22 is an enlarged cross-sectional view taken along the line 22—22 in FIG. 21.
FIG. 23 is a side view of the floss winding portion of the holder of FIG. 20.
FIG. 24 is a view similar to that of FIG. 23 but illustrating the winding portion as seen from the side of the dental floss holder opposed to the side illustrated in FIG. 23.
FIG. 25 is a partial, cross-sectional, elevation view illustrating a cartridge employable in the dental holder system to supply dental floss to the holder.
FIG. 25A is a cross-sectional view taken along the line 25A—25A of FIG. 25.

Positioned adjacent to the securement member 80 and rotatable relative thereto and relative to the holder elements of the holder is a floss engaging and winding member 88 defining a circular-shaped outer groove 90. The outer wall of member 88 is in the form of a disc segment and forms floss engaging surfaces 92. Pawl 86 is pivotally mounted on floss engaging and winding member 88.

In this arrangement one end of the floss 18 is tied down on (secured to) securement member 80, the latter defining a circular groove for accommodating the floss. The floss is then passed under one of the floss engaging surfaces of the member 88 (the left most floss engaging surface when viewed in FIG. 20) and then wrapped about member 88 within the groove 90 in a clockwise fashion.

The floss then extends upwardly along, between, and down along the holder elements as previously described and as shown in FIG. 20. The floss is then passed under the right hand floss engaging surface (as viewed in FIG. 20) and wrapped about securement member 80 clockwise to secure same in position. In this arrangement securement member 80 has the ability to move clockwise (as viewed in FIG. 20) independently of member 88. However, the above described pawl mechanism does not allow the securement member 80 to move counter clockwise.

When the user wishes to advance floss between the holder elements to replace a soiled segment with a clean segment the user rotates securement member 80 and floss engaging and winding member 88 simultaneously (in a clockwise direction as viewed in FIG. 20). As the user flosses, the distal ends of the floss-holding ends thereof separate gradually when maintaining the floss taut due to stretching of the floss.

When the user feels that the floss-holding ends are too far apart and wishes to narrow the length of taut floss in between, this is accomplished by the user ratcheting securement member 80 clockwise with handle 82 while holding floss engaging and winding member 88 stationary. Passage of the pawl over a couple of the ratchet wheel teeth will tighten the floss and attain the desired distance between the floss-holding ends.

FIGS. 25 and 25A disclose a dental floss container or cartridge which may be utilized with any of the dental floss holders of the type illustrated and described above in which a pivot member, such as a pivot member 14, interconnects two holder elements. This could be accomplished simply by forming the pivot member of two selectively separable components, one component being in the form of a stub shaft and the other component defining a socket for receiving the stub shaft. Referring briefly to FIGS. 1 and 2, the projection 16, for example, could be affixed to a stub shaft and that portion of the pivot member 14 positioned on the other side of the holder elements could define a socket for retaining the stub shaft in position. If the stub shaft were made long enough it could be utilized as a support for the cartridge shown in FIGS. 25, 25A.

The cartridge is designated by reference numeral 102. The circular flat walls of the cartridge, walls 104, 106, define aligned openings which could be utilized to accommodate a mounting stub shaft 108. A wound coil of dental floss 18 is disposed within the interior of the cartridge and the leading end thereof passes through a dental floss exit opening 110 formed in wall 106. After passing outwardly of the dental floss exit opening, the dental floss extends to a dental floss cutter member 112 of the well known type employing an inclined cutter blade.

The wall 106 defines a concavity between the dental floss exit opening and the dental floss cutter member to facilitate manual access to the floss extending thereover so that the floss can be pulled and re-cut. If desired, the outer periphery of the cartridge could form one or more winding grooves and function to simultaneously unwind and wind floss upon rotation, similar to the arrangements shown in FIGS. 16–19B and FIGS. 20–24.

FIGS. 26 through 33 illustrate another form of dental floss holder utilized in a dental floss system which also incorporates novel dental floss and a dental floss container of unique construction. In this embodiment the dental floss holder incorporates pivoted holder elements in the manner of the previously described embodiments. In this embodiment, however, the slots at the distal ends of the holder elements, slots 112, 114, are in communication with sockets 116 of substantially hemispherical configuration. The sockets are formed in the outer sides of the floss-holding ends.

Figures 26, 27, 28, 29:
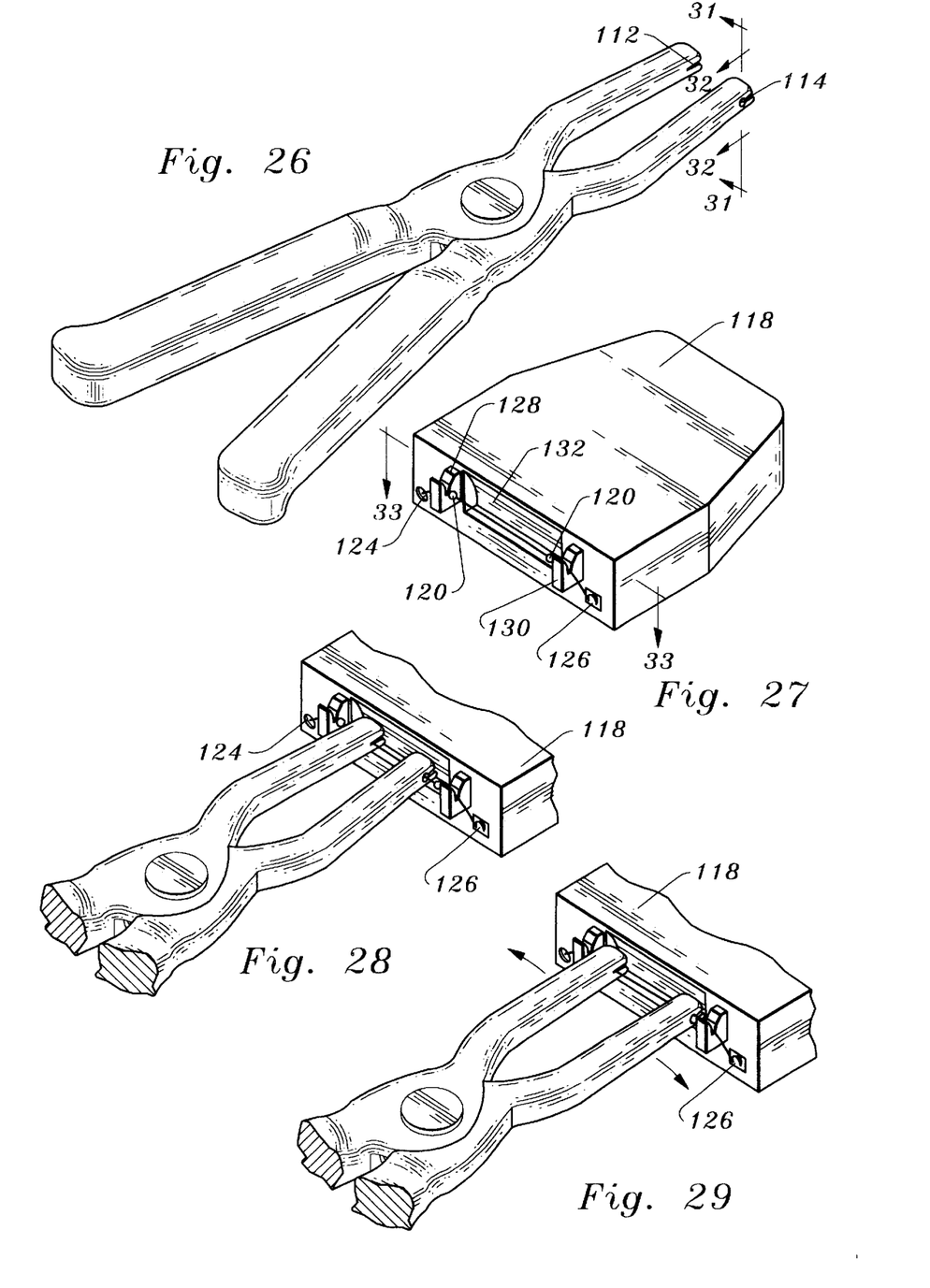
FIG. 26 is a perspective view illustrating a fifth embodiment of dental floss holder constructed in accordance with the teachings of the present invention.
FIG. 27 is a perspective view of a container for dental floss constructed in accordance with the teachings of the present invention illustrating a segment of the dental floss in position for engagement by the dental floss holder of FIG. 26.
FIG. 28 illustrates the dental floss holder of FIG. 26 applied to the dental floss of the container preparatory to removing floss from the container.
FIGS. 29 and 30 illustrate sequential steps being carried out when removing the dental floss from the container with the dental floss holder.

Dental floss container 118 defines a container interior for holding a supply of wound dental floss of a special character. More particularly, the dental floss comprises a length of flexible dental floss material having a plurality of spaced enlargements 120 formed thereon. The flexible component of the dental floss is designated by reference numeral 122 and may be of any suitable material. Likewise, the enlargements 120 may themselves be of any suitable material. Of course, the materials of the two floss components must be compatible so as to allow the enlargements to be fixed in place.

Figure 32:
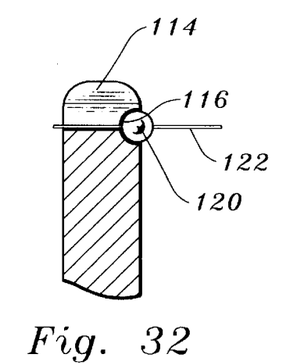
FIG. 32 is an enlarged, partial sectional view as taken along the line 32—32 in FIG. 26, illustrating a segment of dental floss held by floss holding ends of the dental floss holder of FIG. 26.

The enlargements 120 have a spherical configuration and are sized to fit in the sockets 116 of the dental floss holder. The enlargements are spaced substantially equidistant from adjacent enlargements along the length of the flexible dental floss material.

The container 118 includes a wall defining a dental floss outlet opening 124 communicating with the container interior. A dental floss cutter member 126 of any suitable type defining a sharpened surface is mounted on the wall defining the dental floss outlet opening and spaced from the dental floss outlet opening.

Two spaced floss engagement members 128, 130 are positioned between the dental floss outlet opening and the dental floss cutter member and define V-shaped notches receiving the floss. Members 128, 130 are for pinching, engaging and supporting dental floss relatively taut between the dental floss outlet opening and the dental floss cutter member.

Figure 33:
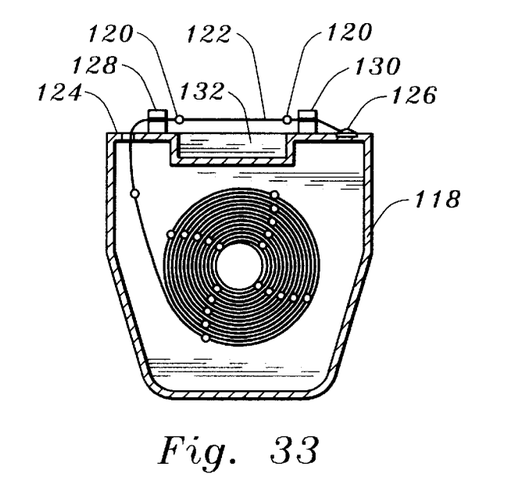
FIG. 33 is a cross-sectional view taken along the line 33—33 of FIG. 27.

FIG. 27 discloses a length of dental floss in position on the floss engagement members 128, 130, the extreme ends of the illustrated section of dental floss being at dental floss outlet opening 124 and at the cutter member 126. As is typical, cutter member 126 may pinch the dental floss strand to maintain it in position. The dental floss extends between the floss engagement members 128, 130 with enlargements 120 positioned adjacent to the inner opposed surfaces thereof. The container 118 defines a concavity 132 lying underneath the floss between the floss engagement members.

One wishing to apply the floss to the dental floss holder maneuvers the dental floss holder as shown in FIG. 28 so that the floss-holding ends thereof are located between the two enlargements. The flexible element of the dental floss is positioned in slots 112, 114.

Next, the dental floss user squeezes together the manually engageable ends of the dental floss holder to move the floss-holding ends apart as shown in FIG. 29 until the enlargements enter sockets 116. Now the operator, while maintaining the floss between the floss-holding ends tightened, removes the floss outwardly from the floss engagement members and pulls additional floss out of outlet opening 124 to reposition a new length of dental floss in the position formerly occupied by the length of dental floss held by the dental floss holder. That is, the new length of dental floss is positioned with the enlargements thereof located next to the opposed inner surfaces of the floss engagement members.

Figure 30:
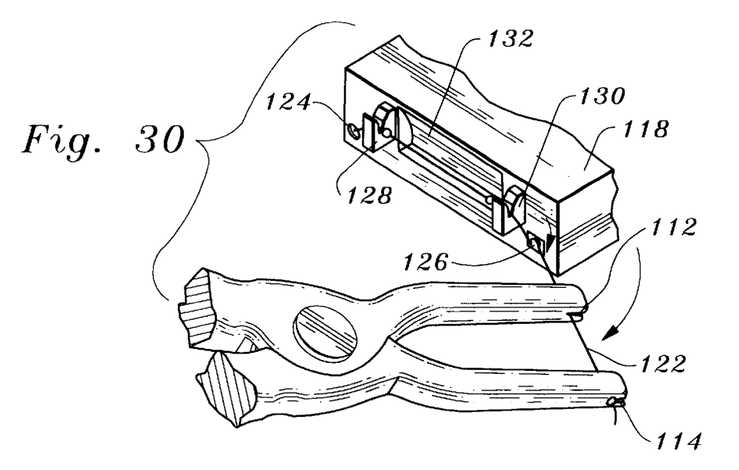
Figure 31:
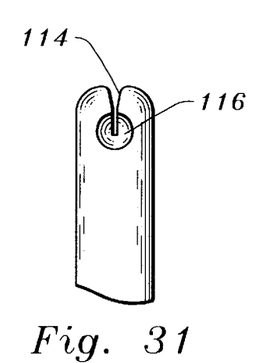
FIG. 31 is an enlarged, side view of that portion of the dental floss holder shown in FIG. 26 as designated by line 31—31 in FIG. 26.

The dental floss holder is maneuvered to cut the floss with the cutter member as shown in FIG. 30, the distal end of the floss remaining on the container being pinched and held in place by the cutter member after cutting of the floss. The members 128, 130 also pinch and hold the remaining floss in place. The concavity 132 provides enough clearance for the ends of the dental floss holder to accomplish the initial floss engagement and pickup.

I claim:

1. A dental floss holder comprising, in combination;
    a double-ended, elongated first holder element including a floss-holding end having a distal end and a manually graspable end;
    a double-ended, elongated second holder element including a floss-holding end having a distal end and a manually graspable end, said first and second holder elements each defining slots at the distal ends of the floss-holding ends thereof for receiving said dental floss and positioning said dental floss so that said dental floss extends between the distal ends of the floss-holding ends of said holder elements;
    pivot means having a pivot axis, at least one of said holder elements being rotatably movable about said pivot axis to vary the distance between the floss-holding ends of said holder elements; and floss securement means located at said pivot means for temporarily securing dental floss to said dental floss holder at spaced locations on said dental floss with said dental floss extending between the floss-holding ends of said holder elements, at least one of said holder elements defining a pair of reserve loop retention slots, the reserve loop retention slots of said pair of reserve loop retention slots being located on opposed sides of the holder element defining the pair of reserve loop retention slots at locations between the distal end of the floss-holding end thereof and said floss securement means, said loop retention slots of said pair of reserve loop retention slots for accommodating and holding in place on said dental floss holder at least one reserve loop of dental floss wrapped about the holder element defining the pair of reserve loop retention slots between the distal end of the floss-holding end thereof and said floss securement means.

2. The dental floss holder according to claim 1 additionally comprising a protruding guide member adjacent to a slot on at least one of said holder elements at the distal end of the floss holding end thereof for bearing against said dental floss when said dental floss is being applied to said dental floss holder to guide said dental floss into the adjacent slot.

3. The dental floss holder according to claim 1 wherein each of said holder elements defines a floss guide notch communicating with the slot at the distal end of the floss-holding end thereof, each said floss guide notch for positioning dental floss extending along its respective holder element and guiding the dental floss into the slot in communication therewith when dental floss is being applied to the dental floss holder, and said slots at the distal ends of the floss-holding ends of the holder elements receiving dental floss from their respective communicating floss guide notches and maintaining the dental floss in position between said spaced locations.

4. The dental floss holder according to claim 1 wherein each of said holder elements defines a pair of slots at the floss-holding end thereof, the slots of each pair of slots being positioned on opposed sides of the holder element defining said pair of slots, said slots of each pair of slots for accommodating a loop of dental floss looping between and about said floss-holding ends and including two spaced, straight dental floss loop segments extending between said floss-holding ends.

5. The dental floss holder according to claim 1 wherein said floss securement means comprises a projection projecting outwardly from one of said holder elements.

6. The dental floss holder according to claim 5 wherein said projection is rotatable relative to the holder element from which said projection projects.

7. The dental floss holder according to claim 6 including lock means for selectively locking said projection against rotatable movement in at least one rotational direction.

8. The dental floss holder according to claim 7 wherein said lock means comprises a ratchet mechanism.

9. The dental floss holder according to claim 5 wherein said projection has an outer peripheral surface defining at least one floss winding groove for receiving wound dental floss.

10. The dental floss holder according to claim 9 wherein the outer peripheral surface of said projection defines at least two floss winding grooves disposed side-by-side.

11. The dental floss holder according to claim 10 wherein said floss winding grooves are substantially circular and have different circumferences.

12. The dental floss holder according to claim 11 wherein said projection is rotatable relative to the holder element from which said projection projects.

13. The dental floss holder according to claim 10 wherein at one of said floss winding grooves is substantially circular in configuration and wherein another of said grooves defines an arc comprising a segment of a circle.

14. The dental floss holder according to claim 10 wherein said projection includes two relatively moveable projection portions, one of said projection portions defining one of said floss winding grooves and the other of said projection portions defining another of said floss winding grooves.

15. A dental floss holder comprising, in combination:
a double-ended, elongated first holder element including a floss-holding end and a manually graspable end;
a double-ended, elongated second holder element including a floss-holding end and a manually graspable end;
pivot means having a pivot axis, at least one of said holder elements being rotatably movable about said pivot axis to vary the distance between the floss-holding ends of said holder elements; and
floss securement means located at said pivot means for temporarily securing dental floss to said dental floss holder at spaced locations on said dental floss with said dental floss extending between the floss-holding ends of said holder elements, said floss securement means comprising a projection projecting outwardly from one of said holder elements, said projection rotatable relative to the holder element from which said projection projects and having an outer peripheral surface defining at least two floss winding grooves disposed side-by-side for receiving wound dental floss, said floss winding grooves being substantially circular and having different circumferences.

16. A dental floss holder comprising, in combination:
a double-ended, elongated first holder element including a floss-holding end having a distal end and a manually graspable end;
a double-ended, elongated second holder element including a floss-holding end having a distal end and a manually graspable end;
pivot means having a pivot axis, at least one of said holder elements being rotatably movable about said pivot axis to vary the distance between the floss-holding ends of said holder elements;
floss securement means located at said pivot means for temporarily securing dental floss to said dental floss holder at spaced locations on said dental floss with said dental floss extending between the floss-holding ends of said holder elements, each of said holder elements defining a pair of slots at the distal end of the floss-holding end thereof, the slots of each pair of slots being positioned on opposed sides of the holder element at the distal end of the floss holding end thereof;
a loop of dental floss looping between and about said floss-holding ends and including two spaced, straight dental floss loop segments extending between said floss-holding ends; and
a protruding guide member adjacent to a slot on at least one of said holder elements for bearing against said dental floss when said dental floss is being applied to said dental floss holder to guide said dental floss into the adjacent slot.

* * * * *